United States Patent
Saito et al.

[11] Patent Number: 5,255,204
[45] Date of Patent: Oct. 19, 1993

[54] METHOD OF CALIBRATING AN ENZYME IMMUNO ASSAY SYSTEM

[75] Inventors: Yukio Saito, Yokohama; Koichi Sekiya, Ciba; Yoshihiro Sato, Yokohama; Takeshi Kohno, Hirakata; Hiroaki Takahasi; Kenji Yamamoto, both of Kyoto, all of Japan

[73] Assignees: Sankyo Company, Ltd., Tokyo; Horiba, Ltd., Kyoto, both of Japan

[21] Appl. No.: 668,780

[22] Filed: Mar. 13, 1991

[30] Foreign Application Priority Data

Mar. 13, 1990 [JP] Japan .................. 2-62191

[51] Int. Cl.⁵ .............................. G06F 15/46
[52] U.S. Cl. ......................... 364/497; 356/36; 364/571.02; 364/571.04
[58] Field of Search ........... 364/496, 497, 498, 571.01, 364/571.04, 571.05, 571.02; 356/36; 436/8

[56] References Cited

U.S. PATENT DOCUMENTS

| | | | |
|---|---|---|---|
| 3,679,312 | 7/1972 | Mansberg | 356/36 |
| 3,825,762 | 7/1974 | White | 250/458.1 |
| 3,986,776 | 10/1976 | George | 364/498 |
| 4,293,222 | 10/1981 | Caruso et al. | 364/498 |
| 4,568,186 | 2/1986 | Yoshimura et al. | 364/498 X |
| 4,587,624 | 5/1986 | Banno | 364/571.04 |
| 4,652,735 | 3/1987 | Ishikawa et al. | 250/578 |
| 4,755,055 | 7/1988 | Johnson et al. | 356/36 |
| 5,014,216 | 5/1991 | Stafford et al. | 364/496 |
| 5,121,443 | 6/1992 | Tomlinson | 364/498 X |

FOREIGN PATENT DOCUMENTS 0355738 2/1990 European Pat. Off. .

*Primary Examiner*—Kevin J. Teska
*Attorney, Agent, or Firm*—Price, Gess & Ubell

[57] ABSTRACT

The present invention relates to a method of measuring a concentration of a substance in an enzyme immuno assay system comprised of two optical detectors and a method of calibrating the same. A calibration curve is prepared by the use of the standard samples having known concentrations to be memorized, the standard samples being measured by the two optical detectors, conversion values of outputs from two optical detectors being determined from the resulting measured values, and the calibration curve being corrected on the basis of the conversion values of outputs to establish a new one-piece continuous calibration curve.

9 Claims, 5 Drawing Sheets

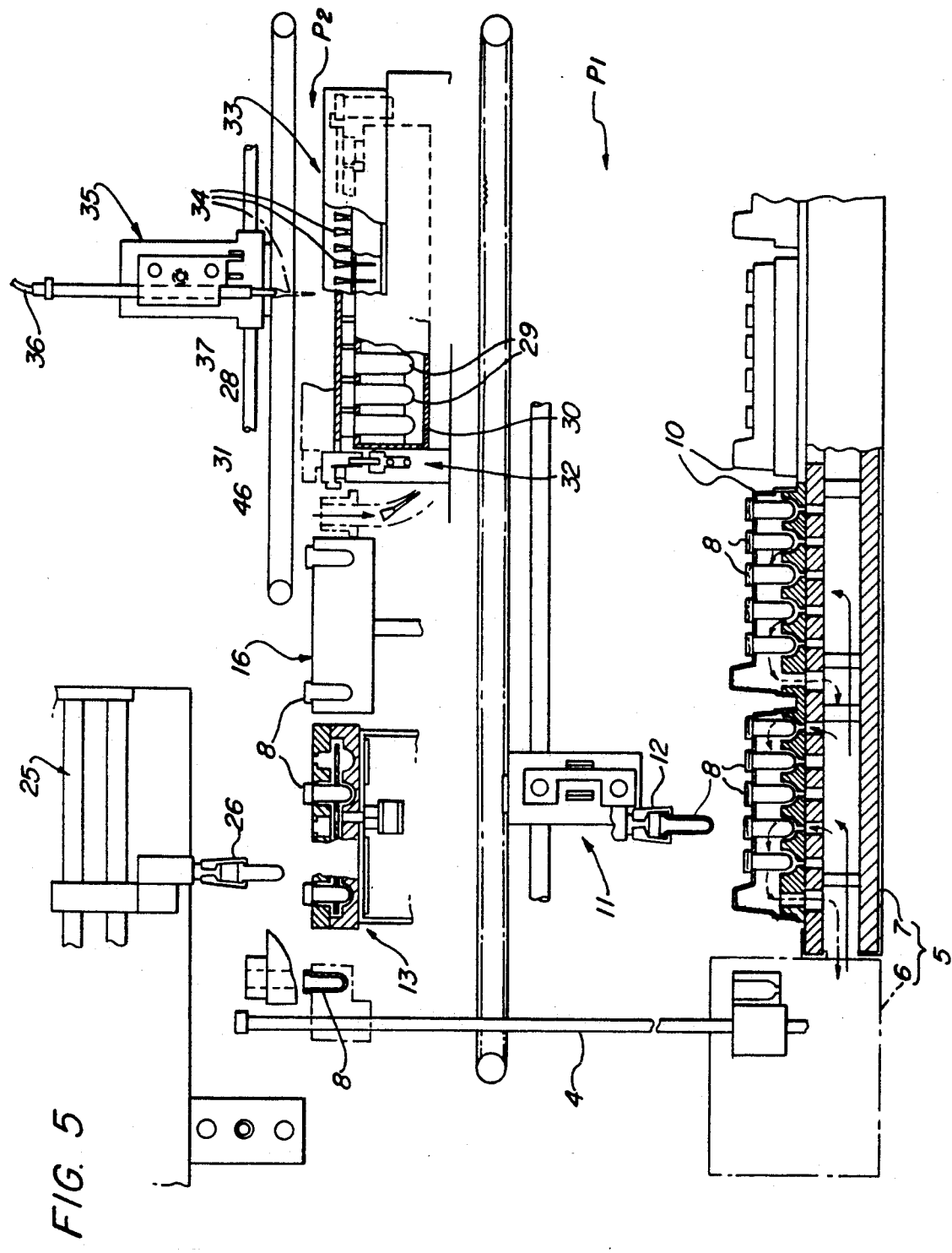

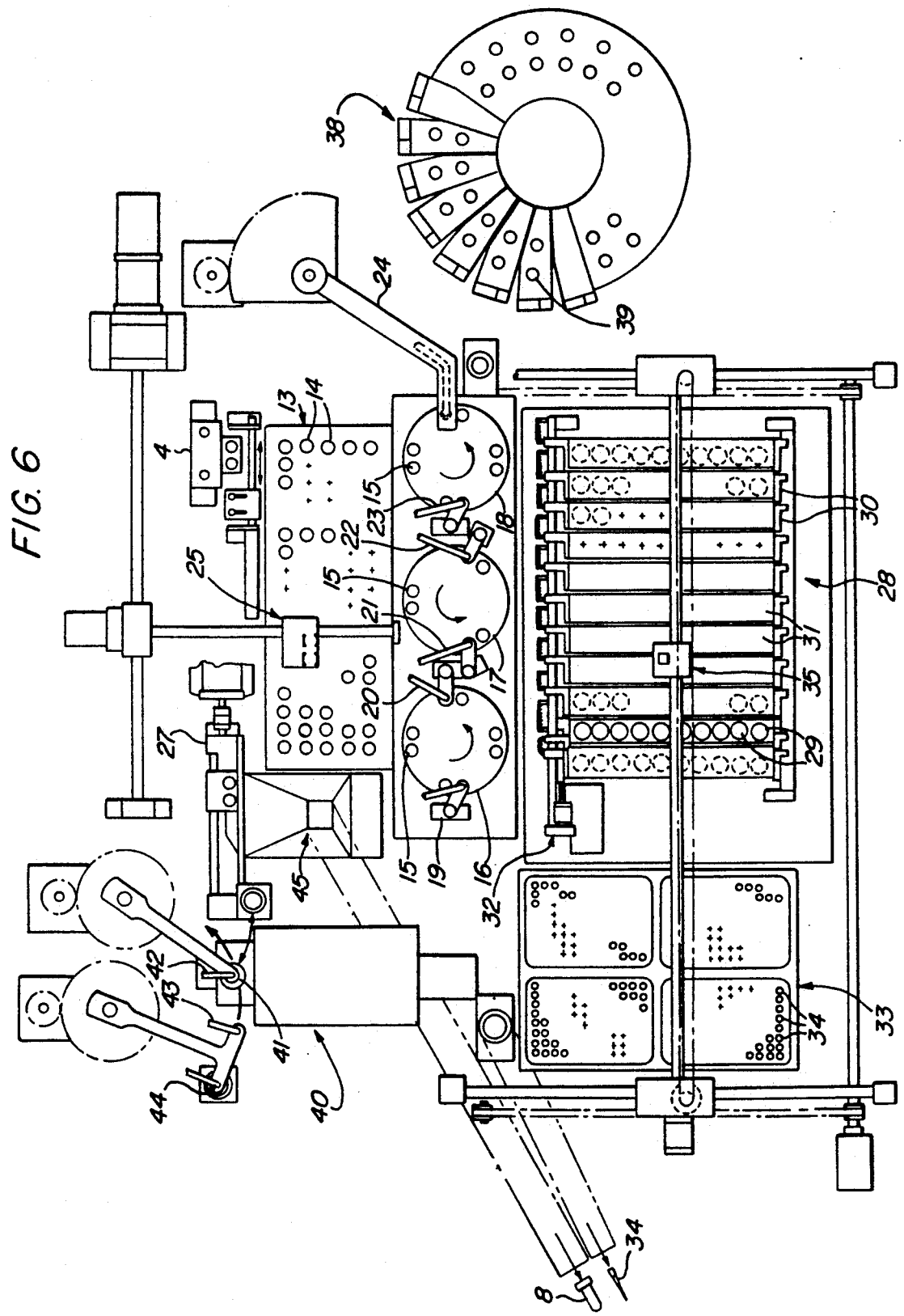

METHOD OF CALIBRATING AN ENZYME IMMUNO ASSAY SYSTEM

BACKGROUND OF THE INVENTION

1. Field of the Invention

The present invention relates to a method of calibrating an enzyme immuno assay system and, in particular, to a method of calibrating an enzyme immuno assay system in which an intensity of a chemical luminescence generated in a photometric cell is detected with two optical detectors having different levels of measurement sensitivity.

2. Description of Related Art

An enzyme immuno assay system measures various substances found in blood, such as carcino embryonic antigen (CEA), ferritin (FER), α-fetoprotein (AFP), and thyroxine binding globulin (TBG). Measurement is accomplished according to the enzyme immuno method, outlined as follows:

A sample (serum) to be measured is put in an antibody immobilized tube with an antibody immobilized therein, and then a suitable enzyme conjugated antibody reagent is added to carry out an immunological reaction. Subsequently, a substrate solution is added to carry out an enzyme reaction, thereby generating a reaction liquid containing hydrogen peroxide A portion of the resulting reaction liquid containing the hydrogen peroxide is then put in a photometric cell, together with a luminescent reagent (luminol), to measure the substances by detecting an intensity of a chemical luminescence generated in said photometric cell.

A conventional chemical luminescence-detecting apparatus is schematically shown in FIG. 7. The conventional apparatus is comprised of a cylindrical photometric cell 91 made of glass or plastic and fixedly mounted on an integrated spherical cell holder 92. A quantity of chemical luminescence generated within the photometric cell 91 is detected by an optical detector photomultiplier tube 94 through a shutter 93, by the so-called batch-type measuring method. A high-voltage power source 95 and an amplifier 96 are also provided.

According to the conventional chemical luminescence-detecting apparatus shown in FIG. 7, only one photomultiplier tube 94 is provided for the photometric cell 91. In the conventional apparatus, it has been necessary to carry out the measurement by regulating the measuring conditions of the photomultiplier tube 94 by various kinds of devices: for example, a supply voltage from said high-voltage power source 95, a value of feedback resistance in said amplifier 96 and the like. Thus, a range in which said quantity of chemical luminescence can be measured is limited because all measurements are carried out under the same condition.

The chemical luminescence method has been recently used to perform enzyme immuno measurement in an enzyme immuno assay. However, because of the inherent range limitation, it has been very difficult to use the above-described conventional chemical luminescence-detecting apparatus for such purpose. The difficulty arises because a large number of items must be randomly measured in the enzyme immuno measurement, resulting in a very wide range in the quantity of light to be measured. The measurement cannot possibly be carried out by means of a single optical detector like that shown in FIG. 7.

The present inventors have made a separate application for patent for an apparatus for detecting a chemical luminescence in which a chemical luminescence generated in a photometric cell is detected by means of a plurality of optical detectors that are different in sensitivity of measurement.

In the case where said apparatus for detecting a chemical luminescence is calibrated by means of, for example, two optical detectors different in sensitivity of measurement, a calibration curve of each optical detector is obtained but outputs from both optical detectors are different in level, so only a noncontinuous calibration curve can be obtained. However, in order to carry out the conversion into concentration over a wide range, a continuous calibration curve is necessary, and the calibration at discontinuous points is also necessary.

SUMMARY OF THE INVENTION

The present invention has been achieved paying attention to the above-described matters. It is an object of the present invention to provide a method of calibrating an enzyme immuno assay system that is simple to accomplish and will provide measurement over a wide range of concentrations.

In order to achieve the above-described object, according to the present invention, in an enzyme immuno assay system adapted to detect an intensity of a chemical luminescence generated in a photometric cell by means of two optical detectors different in sensitivity of measurement, a calibration curve is prepared by the use of standard samples having known concentrations to be memorized, one of said standard samples being measured by said two optical detectors, conversion values of outputs from the two optical detectors being determined from the resulting measured values, and said calibration curve being corrected on the basis of said conversion values of outputs to establish a continuous one-piece calibration curve.

According to the method of the present invention, a continuous one-piece calibration curve can be obtained for use over a wide range of concentrations, so that the apparatus can be used, under the same conditions, to measure various items contained in blood at various concentrations.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

One preferred embodiment of the present invention is shown in FIGS. 1 to 7, in which:

FIGS. 4 to 6 show an exemplary enzyme immuno assay system incorporating the chemical luminescence-detecting apparatus of FIG. 1, where FIG. 5 is the whole perspective view showing the inside of said system; FIG. 6 is a partially cutaway elevational view of an interior portion of said system; FIG. 7 is a schematic block diagram of a conventional chemical luminescence-detecting apparatus;

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a method of calibrating an enzyme immuno assay system.

Figure 1:
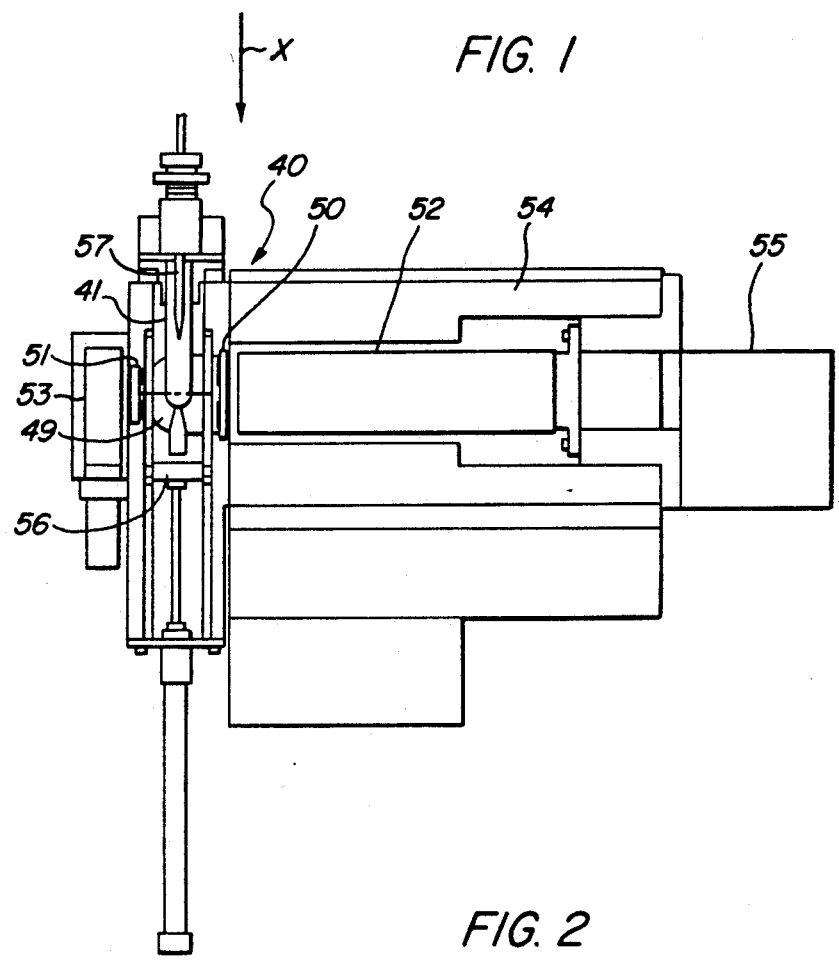
FIG. 1 is a sectional view of a preferred chemical luminescence-detecting apparatus according to the present invention.
Figure 4:
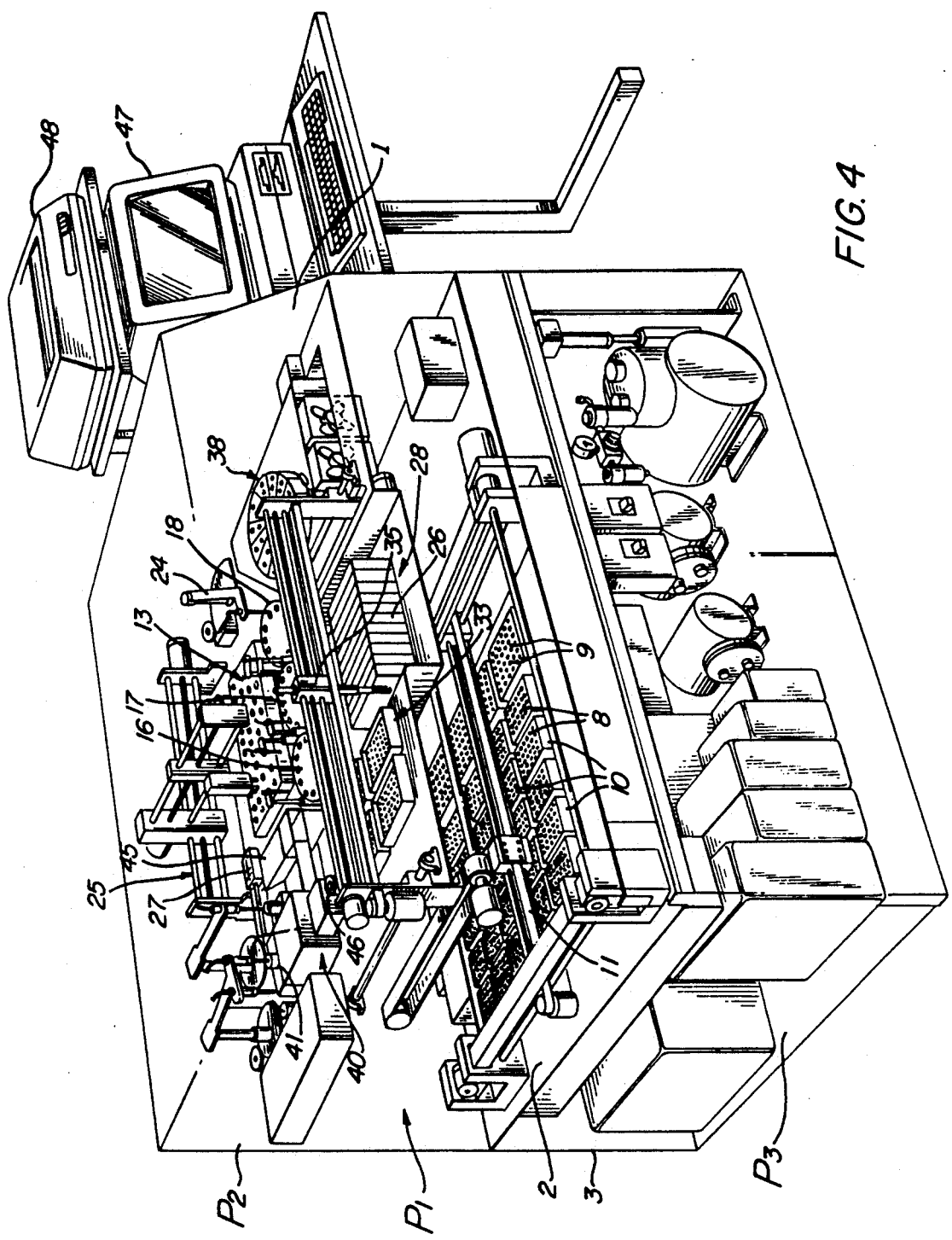

FIG. 1 illustrates a preferred chemical luminescence-detecting apparatus according to the present invention. FIGS. 4 to 6 depict the general construction of an enzyme immuno assay system in which the preferred chemical luminescence-detecting apparatus of FIG. 1 is employed.

As shown in FIG. 4, the enzyme immuno assay system is comprised of partition plates 1, 2 that divide an inner space of an apparatus case into three spaces: a central space $P_1$, an upper space $P_2$, and a lower space $P_3$. The central space $P_1$ is principally comprised of a test tube cooling device 5 that includes a suction exhaust portion 6 connected between a cooling case 7 and a cooler (not shown) provided in the lower space $P_3$. A plurality of test tube support cases 10, having aperture bottoms, are detachably placed on an upper surface of the cooling case 7. Reference numeral 8 designates "antibody test tubes" having an antibody immobilized on an inside thereof and sealed with aluminum foil. Reference numeral 9 designates dilution test tubes (shown in FIG. 4).

As shown in both FIGS. 4 and 5, a first horizontal tube conveying mechanism 11 having a test tube chuck 12 is provided for conveying the antibody test tubes 8 (and the dilution test tubes 9 if needed) to a lower end of a test tube elevator 4. The test tube elevator 4 ranges from a lower end in the central space $P_1$ to an upper end in the upper space $P_2$.

The upper space $P_2$ includes a constant temperature shaker 13 having a plurality of apertures 14 and first to third rotors 16, 17, 18 having apertures 15. The apertures 14, 15 are sized for insertion of the antibody test tubes 8. As shown in FIG. 6, a washer 19 and a diluent dispenser 20 are arranged above the first rotor 16; a washer 21 and a substrate solution dispenser 22 are arranged above the second rotor 17; and a washer 23 and an enzyme conjugated antibody reagent dispenser 24 are arranged above the third rotor 18. The rotors 16, 17, 18 may be rotated in an appointed direction as shown, for example, by the arrows in FIG. 6.

A second horizontal tube conveying mechanism 25 having a test tube chuck 26 is provided in the upper space $P_2$ for conveying the antibody test tubes between any one of the test tube elevator 4, the constant temperature shaker 13, first to third rotors 16, 17, 18, and a sample portion 27.

The upper space $P_2$ further comprises a sample tube storage portion 28 including a plurality of sample tube cases 30, each sample tube case 30 housing a plurality of individual sample tubes 29. A plurality of covers 30 and a cover member closing mechanism 32 are provided to selectively close the upper openings of the sample tube housing cases 30. As explained further herein, a sample, such as serum, may be poured in the sample tubes 29 in the left and right direction, as suggested in FIGS. 5 and 6.

Also provided is a supply area 33 of pipette tips 34, located adjacent to the sample tube housing portion 28. As shown in FIGS. 5 and 6, a sample dispensing mechanism 35, including a freely elevatable probe 37 connected to a suction pipe 36, is movable in two horizontal directions over any one of the pipette supply area 33, the sample tube housing portion 28, and the first rotor 16. A pipette tip 34 may be placed on a lower end of the probe 37 through a descending movement of the probe 37 within the pipette stock area 33. A sample from one of the sample tubes 29 may then be sucked into the pipette tip 34 while the sample dispensing mechanism 35 is above the sample tube housing portion 28, and then the sample may be discharged in an antibody test tube 8 held in the first rotor 16 after locating the sample dispensing mechanism 35 above the first rotor 16.

The upper space $P_1$ is further comprised of a reagent bottle supplier 38 having a plurality of reagent bottles 39 containing the enzyme conjugated antibody reagent.

A photometric portion 40 provided with a glass tube photometric cell 41 is provided adjacent to the sample portion 27. A reactant dispenser 42 is provided for transferring a reactant in the antibody test tube located in the sample portion 27 into the photometric cell 41. A reagent dispenser 43 is provided for pouring a luminescent reagent (for example, luminol solution) into the photometric cell 41, and a washer 44 is provided for cleansing the photometric cell 41. First and second chutes 45, 46 are provided to respectively transporting a previously-used antibody test tube 8 and pipette tip 34 to the outside.

The system of the just-described construction may be used to implement an enzyme immuno assay with, for example, the two-step sandwich method, as follows:

The antibody test tube 8 containing the antibody to be measured is taken from the central space $P_1$ to an aperture 15 of the first rotor 16 via the first horizontal test tube conveying mechanism 11, the test tube elevator 4, and the second horizontal test tube conveying mechanism 25. The aluminum foil sealing the upper opening of the antibody test tube 8 is broken in the process of transporting the antibody test tube 8. The antibody test tube 8 is deposited in an aperture 15 of the first rotor 16.

The probe 37 is then provided with a new pipette tip 34 at a lower end thereof. The probe 38 and the pipette tip 34 are positioned over a sample tube 29 so that a sample contained therein may be sucked into the pipette tip 34 and then poured into the antibody test tube 8 located in the first rotor 16. After the sample has been poured into the antibody test tube 8, the pipette tip is discarded via shoot 46.

The first rotor 16 is rotated a predetermined amount, and then a diluent is poured into the antibody test tube 8 from the diluent dispenser 20. The antibody test tube is then moved into the constant temperature shaker 13 and shook for an appointed time at body temperature to carry out a first immuno reaction.

The antibody test tube is then moved to the second rotor 17 to be washed and then subjected to a so-called B/F separation. An appointed amount of substrate solution corresponding to the item to be measured is then poured into the antibody test tube 8 from the dispenser 22. The antibody test tube 8 is then moved back to the constant temperature shaker 13 to carry out a second immuno reaction.

The antibody test tube is now moved to the third rotor 18 to be washed and to then have an appointed quantity of enzyme conjugated antibody reagent poured therein from dispenser 24. The antibody test tube is returned to the constant temperature shaker 13 for a third time to carry out an enzyme reaction, during which reaction hydrogen peroxide is generated in a quantity corresponding to the quantity of the substance to be measured by this reaction.

After the enzyme reaction, the antibody test tube 8 is conveyed with the second horizontal test tube conveying mechanism 25 to the sample portion 27. The reaction solution containing hydrogen peroxide in the antibody test tube 8 is then added to the photometric cell, into which the luminescent reagent was previously poured, to carry out a luminescent reaction. The antibody test tube 8 is then discarded via shoot 45.

During the above-described luminescent reaction, a luminescent quantity is electrically measured with the assistance of a computer, and then the concentration of the luminescent substance is displayed as an analytical result on a monitor 47 or a printer 48.

The photometric portion of the above-described enzyme immuno assay system is shown in more detail in FIG. 1. As shown, the photometric cell 41 is held by a cell holder 49 having an integrated spherical shape. An interference filter 50 and a high sensitivity photomultiplier tube ("HPMT") 52 is disposed on one side of the photometric cell, and an interference filter 51 and a low sensitivity photomultiplier tube ("LPMT") 53 is disposed on the other side. The HPMT 52 and the LPMT 53 are disposed in a straight line, as seen from the direction of an arrow X. The HPMT 52 includes a housing 54 provided with a cooler (not shown) for reducing the dark current. Also provided are an amplifier 55 for the HPMT 52, a shutter 56, and a reactant pouring nozzle 57.

Figure 2:
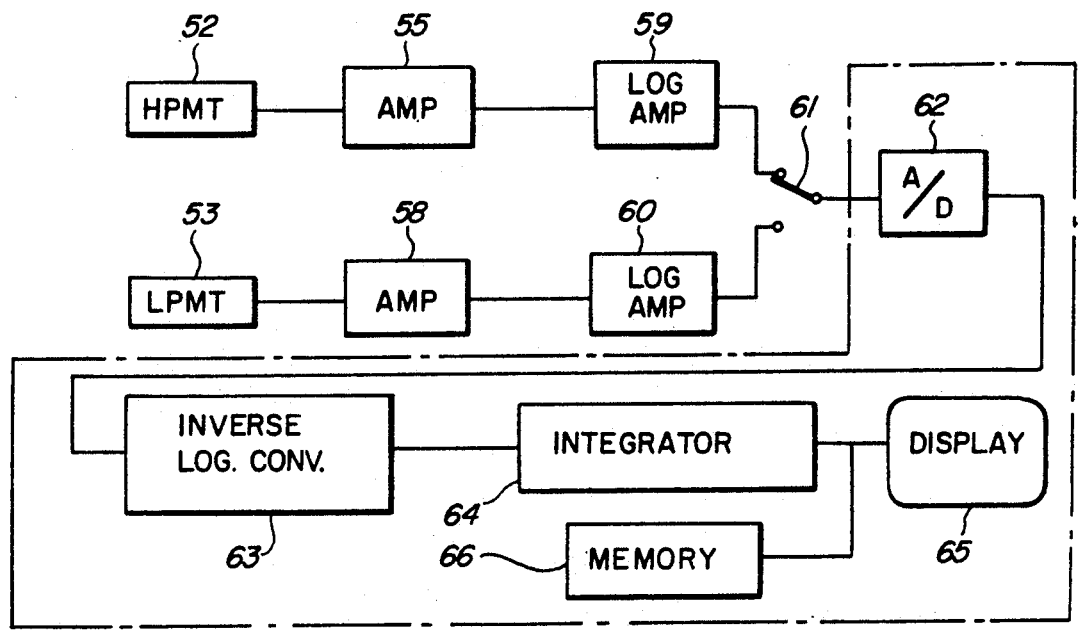
FIG. 2 is a schematic block diagram showing the construction of a circuit used with the apparatus of FIG. 2.

Because the sensitivity of the HPMT 52 is vastly different from that of the LPMT 53, an output signal of the HPMT 52 is at a vastly different level than an output signal from the LPMT 53 for the same measured quantity Thus, a concentration signal may only be obtained by separately converting the respective output signals into a signal quantity, as shown by the construction of FIG. 2.

FIG. 2 schematically depicts the connections between the HPMT 52 and the LPMT 53. Included are amplifiers 55, 58, log amplifiers 59, 60, changeover switch 61, A/D converter 62, inverse log converter 63, integrator 64, display 65, and memory 66.

The log amplifiers 59, 60 and the inverse log converter 63 are not always required, depending upon the measuring range and the range of the A/D converter 62. It is to be further understood that the position of the changeover switch 61 is not limited to that shown. For example, if two A/D converters were used, one each for the HPMT 52 and the LPMT 53, then the switch 61 may be disposed on the output sides of the two A/D converters.

The changeover switch 61 is an analog switch for dividing the data by alternately providing the output signal from the HPMT 52 and the output signal from the LPMT 53 to the A/D converter 62 every 50 msec.

In this preferred embodiment, the radiant life is usually about 10 seconds and, as above described, the output from the detector is alternately taken from the LPMT 563 and the HPMT 52 every 50 msec, so that finally the output from the respective detectors is divided into 200 pieces to be put in the computer. (The integral value of the respective outputs becomes the datum adopted in the operation of concentration.) The signal from the HPMT 52 and the signal from the LPMT 53 are digitized by the A/D converter 62 and stored in the computer. At this time, the signal from the HPMT 52 is preferentially adopted as the datum for the operation of concentration and, in the case where the signal from the HPMT 52 exceeds the regulation current, the signal from the LPMT 53 is adopted. If the output of the LPMT 53 is to be used, its output is multiplied by a factor determined by a ratio of the HPMT 52 output to the LPMT 53 output that was determined in previously-determined luminescent intensities.

Figure 3:
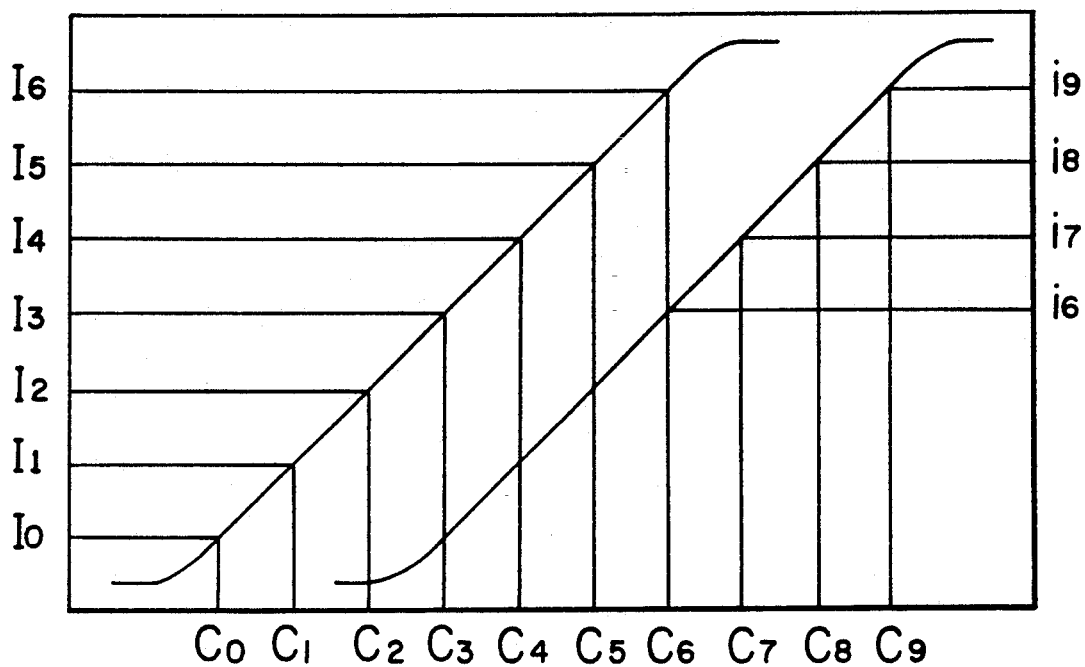
FIG. 3 is a schematic diagram showing the relationship between a concentration of luminous substances and respective outputs from a high sensitivity photomultiplier tube and a low sensitivity photomultiplier tube.
Figure 7:
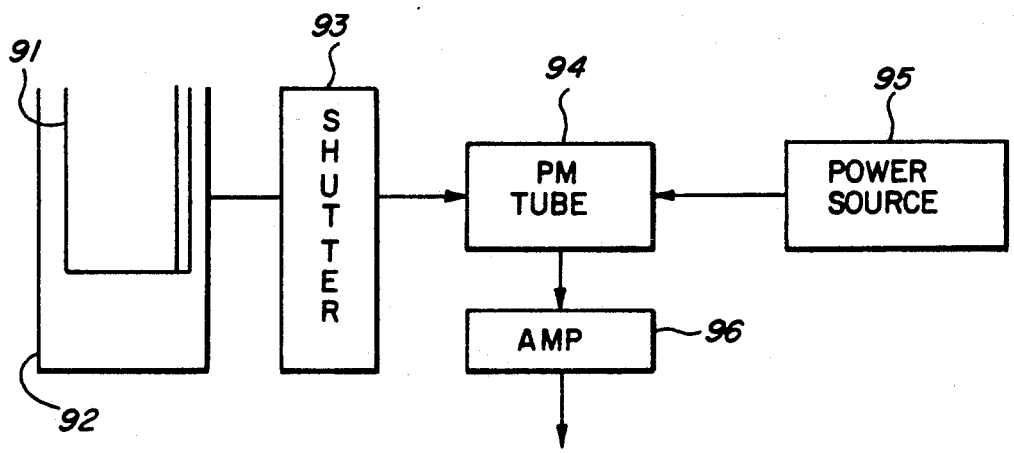
FIG. 7 is an overhead plan view showing the main components of said system.

The graph of FIG. 3 depicts the relationship between the output of the HPMT 52 and the output of the LPMT 53 as a function of a concentration of a luminescent substance $C_0$ to $C_9$. The designation $I_0$ to $I_6$ on the left side of the ordinate designate the output of the HPMT 52 for concentrations $C_0$ to $C_6$, and the designations $i_6$ to $i_9$ on the right side of the ordinate designate the output from the LPMT 53 for concentrations $C_6$ to $C_9$. Accordingly, the ratio ("A") of the HPMT 52 output to the LPMT 53 output based on the luminescent intensities $C_e$ to $C_9$ can be determined.

For example, provided that the HPMT 52 output is $I_r$ and the LPMT 53 output is $i_r$, the ratio A can be determined as $I_r/i_r$. Thus, it may be detected by means of the LPMT 53 that the output from the HPMT 52 has saturated, and then an output i from the LPMT 53 may be converted, with the expression $I = i \times A$, into an output I equivalent to that from the HPMT 52 were it not saturated.

As described below and with reference to FIG. 3, a plurality of standard serums having known concentrations are used for preparing the calibration curve and a regression (method of establishing the new calibration curve).

(1) In the case where the concentrations of the standard serums range from $C_0$ to $C_2$,
  the calibration curve is prepared by the use of data $I_0$ to $I_2$ of the HPMT 52. But in the case where the output of the HPMT 52 exceeds the regulation value of current, the conversion value of the output of the LPMT 53 is determined by the use of the output ratio, which has been previously determined before the measurement, and the regression is carried out by the use of the outputs of the HPMT 52 at the respective concentrations and the conversion values of the output to prepare the calibration curve, thereby calculating the concentration from the calibration curve.

(2) In the case where the concentrations of the standard serums range from $C_0$ to $C_6$, the calibration curve is prepared by the use of data $I_0$ to $I_6$ of the HPMT 52. But in the case where the output of the HPMT 52 exceeds the regulation value of current, the conversion value of the output of the LPMT 53 is determined by the use of the output ratio $I_6/i_6$ determined at $C_6$, and the calibration curve is prepared in the same manner as in the above-described (1) to calculate the concentration from this calibration curve.

(3) In the case where the concentrations of the standard serums range from $C_2$ to $C_7$, the calibration curve is prepared by first converting the output signal $i_7$ of the LPMT 53 into an output of the HPMT 52 using the conversion value $I_6/i_6$ determined at $C_6$. The calibration curve is then prepared in the same manner as in the above-described (1) to calculate the concentration from this calibration curve.

(4) In the case where the concentrations of the standard serum range from $C_6$ to $C_9$, the calibration curve is prepared by the use of data $i_6$ to $i_9$ of the LPMT 53. But in the case where the output of the LPMT 53 is below the regulation value of current, the conversion values of the output of the LPMT 53 are determined by the use of the output ratios which have been previously determined before the measurement, and the regression is carried out by the use of the outputs of the HPMT 52 at the respective concentrations and the conversion values of the output to prepare the calibration curve, thereby calculating the concentration from this calibration curve. The conversion values of the output of the LPMT 53 are determined by the use of the output ratios which have been previously determined before the measurement.

(5) In the case where the concentrations of the standard serums range from $C_7$ to $C_9$, the calibration curve is prepared by the use of data $i_7$ to $i_9$ of the LPMT 53. But in the case where the output of the LPMT 53 is below the regulation value of current, the conversion value of the output of the LPMT 53 is determined by the use of the output ratio, which has been previously determined before the measurement, and the regression is carried out by the use of the outputs of the LPMT 53 at the respective concentrations and the conversion values of the output to prepare the calibration curve, thereby calculating the concentration from the calibration curve.

As described above, the methods of preparing the calibration curve are different, depending upon the concentration range of the standard serums, but a continuous one-piece calibration curve can be obtained in every case.

The equation for calculating the concentration can be expressed as a function of the output I of the HPMT 52 or of the output of the LPMT 53 converted into the output I of the HPMT 52:

$$C = f(I)$$

But in the calibration at one point, the new coefficient $A'$ is determined from the following equation:

$$I_r'/i_r' = A'$$

and if the conversion value $I'$ obtained by reconverting the preceding output $i$ of the LPMT 53 by the coefficient $A'$ is expressed by the following equation:

$$I' = i \times A'$$

the new equation for calculating the concentration is expressed by the following equation:

$$C = f(I')$$

As described above, according to the present invention, one piece of continuous calibration curve can be obtained over a wide range of concentrations, so that the apparatus can be calibrated so that the respective items contained in blood of various concentrations can also be measured under the same conditions.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method of measuring a concentration of a sample contained in a photometric cell comprising the steps of:
   (a) providing a first optical detector of a first sensitivity for providing a first output value corresponding to a first range of concentrations adjacent said photometric cell;
   (b) providing a second optical detector of a second sensitivity different than the first sensitivity for providing a second output value corresponding to a second range of concentrations adjacent said photometric cell, said second range of concentrations including a overlapping range that partially overlaps said first range of concentrations;
   (c) automatically exciting said sample to a luminescent reaction to emit light;
   (d) measuring said luminescent light with said first optical detector to provide an electrical first output value;
   (e) measuring said luminescent light with said second optical detector to provide an electrical second output value;
   (f) determining an output ratio of said first and second outputs for a particular concentration that lies within said overlapping range of concentrations;
   (g) preparing a calibration curve for converting said first and second output values into said concentration of said sample;
   (h) determining if one of said optical detectors is beyond its range of concentrations; and
   (i) deriving said concentration of said sample with said calibration curve if one of said optical detectors is beyond its range of concentrations based on a product of said other output value multiplied by said output ratio.

2. The method of claim 1 wherein said calibration curve includes a first portion corresponding to said first optical detector and a second portion corresponding to said second optical detector and wherein the step of preparing a calibration curve is comprised of the further steps of:
   (i) measuring a plurality of first output values corresponding to a plurality of standard samples having known concentrations that are exclusively within said first range of concentrations; and
   (ii) determining said first portion of said calibration curve based on said first output values and determining said second portion of said calibration curve based on said first output values and a last determined output ratio of said first and second output values.

3. The method of claim 1 wherein said calibration curve includes a first portion corresponding to said first optical detector and a second portion corresponding to said second optical detector and wherein the step of preparing a calibration curve is comprised of the further steps of:
(i) measuring:
(a) a plurality of first output values corresponding to a plurality of standard samples having known concentrations that are exclusively within said first range of concentrations; and
(b) a first and second output value corresponding to a standard sample having a known concentration that is within said overlapping range;
(ii) determining a new output ratio of said first and second outputs corresponding the standard sample having a known concentration that is within said overlapping range; and
(iii) determining said first portion of said calibration curve based on said first output values of said first optical detector and determining said second portion of said calibration curve based on said new output ratio.

4. The method of claim 1 wherein said calibration curve includes a first portion corresponding to said first optical detector and a second portion corresponding to said second optical detector and wherein the step of preparing a calibration curve is comprised of the further steps of:
(i) measuring:
values corresponding to a plurality of standard samples having known concentrations that are exclusively within said first range of concentrations;
(b) a first and second output value corresponding to a standard sample having a known concentration that is within said overlapping range; and
(c) a second output value corresponding to a standard sample having a known concentration that is exclusively within said second range of concentrations;
(ii) determining a new output ratio of said first and second outputs corresponding to the standard sample having a known concentration that is within said overlapping range;
(iii) multiplying said second output value corresponding to a standard sample having a known concentration that is exclusively within said second range of concentrations by the new output ratio to provide a virtual output value of the first optical detector; and
(iv) determining said first portion of said calibration curve based on said first output values of said first optical detector and said virtual output value and determining said second portion of said calibration curve based on said new output ratio.

5. The method of claim 1 wherein said calibration curve includes a first portion corresponding to said first optical detector and a second portion corresponding to said second optical detector and wherein the step of preparing a calibration curve is comprised of the further steps of:
(i) measuring:
(a) a first and second output value corresponding to a standard sample having a known concentration that is within said overlapping range; and
(b) a plurality of second output values corresponding to a plurality of standard samples having known concentrations that are exclusively within said second range of concentrations;
(ii) determining a new output ratio of said first and second outputs corresponding to the standard sample having a known concentration that is within said overlapping range; and
(iii) determining said second portion of said calibration curve based on said second output values and determining said first portion of said calibration curve based on said second output values and a last determined output ratio of said first and second output values.

6. The method of claim 1 wherein said calibration curve includes a first portion corresponding to said first optical detector and a second portion corresponding to said second optical detector and wherein the step of preparing a calibration curve is comprised of the further steps of:
(i) measuring a plurality of second output values corresponding to a plurality of standard samples having known concentrations that are exclusively within said second range of concentrations; and
(ii) determining said second portion of said calibration curve based on said second output values and determining said first portion of said calibration curve based on said second output values and a last determined output ratio of said first and second output values.

7. The method of claim 1 wherein the concentration derived in said step of deriving is based on said first output value if said first optical detector has not saturated and is based on the product of said second output value multiplied by said output ratio if said first optical detector has saturated.

8. An enzyme immuno assay system for measuring a concentration of a substance contained in blood by an immunological reaction with a sample of the reaction positioned in a phhotometric cell, comprising:
means for automatically introducing the sample into said photometric cells;
a first optical detector of a first sensitivity positioned adjacent said photometric cell for measuring a characteristic light from said sample for providing a first output value corresponding to a first range of concentrations;
a second optical detector of a second sensitivity, lower than the first sensitivity, positioned adjacent said photometric cell for measuring said characteristic light from said sample for providing a second output value corresponding to a second range of concentrations, said second range of concentrations including an overlapping range that partially overlaps said first range of concentrations;
means for determining an output ratio of said first and second outputs for a particular concentration that lies within said overlapping range of concentrations;
means for determining if one of said optical detectors is saturated; and
means for determining the concentration, when one of said optical detectors is saturated, by multiplying said output value of said other optical detector by said output ratio.

9. The system as claimed in claim 8 further including means for periodically and alternatively sampling the first and second output values in order to integrate their discrete sample values into final first and second output values.

* * * * *